US009632091B2

(12) United States Patent
Atwal et al.

(10) Patent No.: US 9,632,091 B2
(45) Date of Patent: Apr. 25, 2017

(54) COMPOSITIONS AND METHODS FOR PROSTATE CANCER ANALYSIS

(71) Applicant: Genentech, Inc., South San Francisco, CA (US)

(72) Inventors: Siminder Atwal, South San Francisco, CA (US); Jo-Anne Hongo, Redwood City, CA (US); Mark Lackner, South San Francisco, CA (US); Elizabeth Punnoose, Hayward, CA (US); Bonnee Rubinfeld, Danville, CA (US); Rajesh Vij, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/919,388

(22) Filed: Oct. 21, 2015

(65) Prior Publication Data
US 2016/0274116 A1 Sep. 22, 2016

Related U.S. Application Data

(63) Continuation of application No. 13/689,407, filed on Nov. 29, 2012, now abandoned.

(60) Provisional application No. 61/703,099, filed on Sep. 19, 2012, provisional application No. 61/629,886, filed on Nov. 29, 2011.

(51) Int. Cl.
*G01N 33/53* (2006.01)
*G01N 33/574* (2006.01)
*C07K 16/30* (2006.01)
*C12N 5/09* (2010.01)

(52) U.S. Cl.
CPC ... *G01N 33/57434* (2013.01); *C07K 16/3069* (2013.01); *C12N 5/0693* (2013.01); *G01N 33/57492* (2013.01); *C12Y 116/01* (2013.01); *C12Y 301/03048* (2013.01); *G01N 2333/4742* (2013.01); *G01N 2333/70596* (2013.01); *G01N 2333/90287* (2013.01); *G01N 2333/916* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,737,456 A | 4/1988 | Weng et al. |
| 4,816,567 A | 3/1989 | Cabilly et al. |
| 5,571,894 A | 11/1996 | Wels et al. |
| 5,587,458 A | 12/1996 | King et al. |
| 5,591,828 A | 1/1997 | Bosslet et al. |
| 5,597,531 A | 1/1997 | Liberti et al. |
| 5,648,237 A | 7/1997 | Carter et al. |
| 5,698,271 A | 12/1997 | Liberti et al. |
| 5,789,199 A | 8/1998 | Joly et al. |
| 5,840,523 A | 11/1998 | Simmons et al. |
| 5,959,177 A | 9/1999 | Hein et al. |
| 6,040,498 A | 3/2000 | Stomp et al. |
| 6,248,516 B1 | 6/2001 | Winter et al. |
| 6,329,503 B1 | 12/2001 | Afar et al. |
| 6,365,362 B1 | 4/2002 | Terstappen et al. |
| 6,417,429 B1 | 7/2002 | Hein et al. |
| 6,420,548 B1 | 7/2002 | Vezina et al. |
| 7,125,978 B1 | 10/2006 | Vezina et al. |
| 2004/0253232 A1 | 12/2004 | Jakobovits et al. |
| 2006/0147951 A1 | 7/2006 | Afar et al. |
| 2007/0160530 A1 | 7/2007 | Jakobovits et al. |
| 2009/0280056 A1 | 11/2009 | Dennis et al. |
| 2010/0111856 A1 | 5/2010 | Gill |

FOREIGN PATENT DOCUMENTS

| | | |
|---|---|---|
| CN | 101258166 A | 9/2008 |
| WO | 93/01161 A1 | 1/1993 |
| WO | 93/16185 A2 | 8/1993 |
| WO | 99/41613 | 8/1999 |
| WO | 99/56779 | 11/1999 |
| WO | 02/086498 A1 | 10/2002 |
| WO | 03/065042 A1 | 8/2003 |
| WO | 2004/025251 A2 | 3/2004 |
| WO | 2005/113601 A2 | 12/2005 |
| WO | 2008/052187 A2 | 5/2008 |
| WO | 2010/028160 A1 | 3/2010 |
| WO | 2011/130566 A2 | 10/2011 |

OTHER PUBLICATIONS

Stott et al (Sci Transl Med, 2010, 2(25): 25ra23, pp. 1-19).*
Racila et al (PNAS, 1998, 95: 4589-4594).*
Almagro et al., "Humanization of antibodies", Frontiers in Bioscience 13:1619-1633 (Jan. 2008).
Challita-Eid et al., "Monoclonal Antibodies to Six-Transmembrane Epithelial Antigen of the Prostate-1 Inhibit Intercellular Communication In vitro and Growth of Human Tumor Xenografts In vivo", Cancer Res 67:5798-5805 (2007).
Cruz et al., "Evaluation of multiparameter flow cytometry for the detection of breast cancer tumor cells in blood samples", Am J Clin Pathol. 123(1):66-74 (2005).
Djulbegovic et al., "Screening for prostate cancer: systematic review and meta-analysis of randomised controlled trials", BMJ 341:c4543 (2010).
English Translation of the First Office Action issued in Chinese Patent Application No. 201280067510.X, dated Apr. 22, 2015 (in 13 pages).
Flatman et al., "Process analytics for purification of monoclonal antibodies", Journal of Chromatography B 848:79-87 ( 2007).
Gerngros, "Advances in the production of human therapeutic proteins in yeasts and filamentous fungi", Nature Biotechnology 22(11):1409-1414 (Nov. 2004).

(Continued)

*Primary Examiner* — Sean Aeder
(74) *Attorney, Agent, or Firm* — Jessica L. Richardson

(57) ABSTRACT

The invention provides methods for diagnosing prostate cancer. The invention also provides novel anti-STEAP-1 antibodies and uses thereof.

17 Claims, 12 Drawing Sheets

(56) References Cited

OTHER PUBLICATIONS

Graham et al., "Characteristics of a human cell line transformed by DNA from human adenovirus type 5", J Gen Virol 36(1):59-72 (Jul. 1977).

Holliger et al., "'Diabodies': Small bivalent and bispecific antibody fragments", P Natl Acad Sci USA 90:6444-6448 (Jul. 1993).

Hubert et al., "STEAP: a prostate-specific cell-surface antigen highly expressed in human prostate tumors", P Natl Acad Sci USA 96(25):14523-8 (1999).

Hudson et al., "Engineered antibodies", Nature Medicine 9(1):129-134 (Jan. 2003).

Israeli et al., "Molecular cloning of a complementary DNA encoding a prostate-specific membrane antigen", Cancer Res. 53(2):227-30 (1993).

Li et al., "Clinical significance of six-transmembrane epithelial antigen of the prostate expressed in prostatic carcinoma", Zhonghua Nan Ke Xue 10(5):351-354 (2004).

Li et al., "Optimization of humanized IgGs in glycoengineered Pichia pastoris", Nat Biotechnol 24(2):210-215 (Feb. 2006).

Liberti et al. In fine particles science and technology "Bioreceptor Ferrofluids: Novel Characteristics and Their Utility in Medical Applications", E. Pelizzetti,:777-90 (1996).

Marrinucci et al., "Case study of the morphologic variation of circulating tumor cells", Hum Pathol. 38(3):514-9 (2007).

Mather et al., "Culture of testicular cells in hormone-supplemented serum-free medium", Ann. NY Acad. Sci. 383:44-68 (1982).

Mather, "Establishment and characterization of two distinct mouse testicular epithelial cell lines", Biol. Reprod. 23:243-252 (1980).

McCall et al., "Phosphorylation of the androgen receptor is associated with reduced survival in hormone-refractory prostate cancer patients", Br J Cancer 98(6):1094-101 (2008).

Pachmann et al., "Quantification of the response of circulating epithelial cells to neodadjuvant treatment for breast cancer: a new tool for therapy monitoring", Breast Cancer Res. 7(6):R975-9 (2005).

Portolano et al., "Lack of promiscuity in autoantigen-specific H and L chain combinations as revealed by human H and L chain 'Roulette'", J Immunol 150(3):880-887 (Feb. 1993).

Reiter et al., "Prostate stem cell antigen: a cell surface marker overexpressed in prostate cancer", P Natl Acad Sci USA 95(4):1735-1740 (Feb. 17, 1998).

Riske et al., "High Affinity Human IgE Receptor (FcεRI). Analysis of functional Domains of the α-Subunit with Monoclonal Antibodies", Journal of Biological Chemistry 266(17):11245-11251 (Jun. 15, 1991).

Search Report issued in Singapore Patent Application No. 11201402711S, dated Apr. 17, 2015, in 4 pages.

Su et al., "Surface-epitope masking and expression cloning identifies the human prostate carcinoma tumor antigen gene PCTA-1 a member of the galectin gene family", Proc Natl Acad Sci U S A 93(14):7252-7 (Jul. 1996).

Tinianow et al., "Site-specifically $^{89}$Zr-labeled Monoclonal Antibodies for ImmunoPET", Nucl Med Biol 37:289-297 (2010).

Urlaub et al., "Isolation of Chinese hamster cell mutants deficient in dihydrofolate reductase activity", Proc. Natl. Acad. Sci USA 77(7):4216-4220 (Jul. 1980).

Verel et al., "$^{89}$Zr Immuno-PET: Comprehensive Procedures for the production of $^{89}$Zr-labeled monoclonal antibodies", J Nucl Med 44(8):1271-1281 (Aug. 2003).

International Search Report issued in International Application No. PCT/US2012/066998, dated Jul. 7, 2013 (in 6 pages).

International Preliminary Report on Patentability issued in International Application No. PCT/US2012/066998, dated Jun. 3, 2014 (in 11 pages).

English translation of Japanese Office Action, pp. 2 (Sep. 28, 2016).

\* cited by examiner

| Source | Patient Number | Cyto-Mem 0 | Cyto-Mem 1+ | Cyto-Mem 2+ | Cyto-Mem 3+ | Membrane Score | Overall Score (0, 1+, 2+, 3+)* |
|---|---|---|---|---|---|---|---|
| Tissue | 101 | 87 | 10 | 3 | 0 | 16 | 1 |
| CTCs | 101 Screening | 2 | 0 | 0 | 0 | 0 | |
| Tissue | 102 | 0 | 0 | 5 | 95 | 295 | 3 |
| CTCs | No screening sample | | | | | | |
| Tissue | 1003 | 0 | 95 | 5 | 0 | 105 | 1 |
| CTCs | 1003 Screening | 2 | 0 | 0 | 0 | 0 | |
| Tissue | 1004 | 20 | 10 | 40 | 30 | 180 | 2 |
| CTCs | 1004 Screening | 10 | 2 | 0 | 2 | 57 | |
| Tissue | 1005 | 0 | 55 | 35 | 10 | 155 | 1 |
| CTCs | 1005 Screening | 37 | 0 | 2 | 2 | 24 | |
| Tissue | 1006 | 0 | 10 | 65 | 25 | 215 | |
| CTCs | 1006 Screening | 23 | 10 | 4 | 0 | 48.6 | |
| Tissue | 1007 | 0 | 75 | 15 | 10 | 135 | 1 |
| CTCs | 1007 Screening | 40 | 5 | 2 | 0 | 19.14 | |
| Tissue | 1008 | 0 | 5 | 10 | 85 | 280 | 3 |
| CTCs | 1008 Screening | 26 | 4 | 6 | 4 | 70 | |
| Tissue | 1009 | 5 | 2 | 28 | 65 | 253 | |
| CTCs | 1009 Screening | 0 | 0 | 0 | 0 | 0 | |
| Tissue | 1010 | | | | | | |
| CTCs | 1010 Screening | 592 | 22 | 0 | 0 | 3.6 | |
| Tissue | 1011 | 10 | 35 | 50 | 5 | 150 | |
| CTCs | 1011 Screening | Not enough blood | | | | | |
| Tissue | 1012 | | | | | | |
| CTCs | 1012 Screening | Failed screening | | | | | |
| Tissue | 1013 | 0 | 0 | 0 | 100 | 300 | |
| CTCs | 1013 Screening | 27 | 2 | 0 | 0 | 6.9 | |

*FIG. 5C*

| | Patient | Pre-dose | Post-dose | |
|---|---|---|---|---|
| Dose 1 | 1 | *2* | 5 | * ← Significant CTC increase by fold change |
| | 2 | 102 | 71 | |
| Dose 2 | 3 | 14 | 24 | |
| | 4 | 41 | 27 | |
| Dose 3 | 5 | 47 | 2 | * ← Significant CTC decrease by fold change |
| | 6 | 40 | 91 | |
| | 7 | *4* | 33 | * ← |
| Dose 5 | 8 | 27 | 22 | |
| Dose 6 | 9 | 446 | 392 | |
| | 10 | 49 | 23 | |
| | 11 | 5 | *1* | * ← |
| | 12 | *4* | 0 | ← |
| Dose 7 | 13 | 93 | *4* | * ← |
| | 14 | 692 | *2* | * ← |

* *Favorable Prognostic Conversion*

* Unfavorable Prognostic Conversion

FIG. 10

COMPOSITIONS AND METHODS FOR PROSTATE CANCER ANALYSIS

RELATED APPLICATIONS

This application is a continuation of U.S. patent application Ser. No. 13/689,407, filed on Nov. 29, 2012, which claims priority under 35 USC 119(e) to U.S. Provisional Patent Application No. 61/629,886, filed Nov. 29, 2011 and U.S. Provisional Patent Application No. 61/703,099, filed Sep. 19, 2012, the contents of which are incorporated herein by reference in their entirety.

FIELD OF THE INVENTION

The present invention relates to the field of oncology and cancer diagnosis, and more specifically to compositions and methods for prostate cancer screening, staging, and treatment monitoring.

BACKGROUND

Prostate cancer is one of the most prevalent cancers in men. While most prostate cancers at early onset are symptom-free and slow growing, certain prostate cancers are more aggressive, painful and lead to fatality. At present, two major types of non-invasive screening tests are available for detection of prostate cancer in men. One is digital rectal exam (DRE), which allows a doctor to detect prostate abnormalities by inserting a gloved finger into the rectum and feeling the prostate gland, and the other is prostate surface antigen test (PSA test), which measures the level of the PSA antigen in a blood sample. Although FDA has approved use of PSA test together with DRE to help detect prostate cancer in men, the PSA test is controversial in screening as it is not clear whether the test actually saves lives. In particular, the United States Preventive Services Task Forces has recently recommended against PSA screening in healthy men, based on findings that PSA screening reduces no or little prostate cancer mortality while leading to treatments or tests that cause unnecessary pain and side effects (see, e.g., R. Chou et al, *Ann. Intern. Med.*, Oct. 7, 2011 E-375; Djulbegovic et al, *BMJ* 2010, 341: c4543). The most definitive diagnosis of prostate cancer is biopsy, where a small piece of the prostate from the suspected patient is removed for microscopic examination for the presence of tumor cells. Obviously such procedure is rather invasive and less desirable in early screening and detection.

As in many other types of cancers, the main cause of death in prostate cancer patients is not the primary tumor but rather the metastasis. Some primary tumor cells can detach themselves from the original tissue and enter into circulation. These cells are called circulating tumor cells (CTCs). Once CTCs seed themselves to a suitable site in the body, they may develop into metastatic colonies that are difficult to detect yet can be life-threatening as they progress into secondary tumors. Attempts have been made to detect the CTCs. However, no methods have been developed that can distinguish if the CTCs are originated from prostate and how the prostate cancer has progressed. In view of the recent finding that PSA screening fails in reducing mortality, there remain significant needs for development of agents and methods that can provide reliable results in the diagnosis and prognosis of prostate cancer.

SUMMARY

In one aspect, the present disclosure provides methods for diagnosing prostate cancer in a test subject, comprising: a) contacting cancer cells of epithelial origin with an antibody that specifically binds to a prostate-specific marker, wherein the cancer cells are from a blood sample taken from the test subject; and b) determining whether any of the cancer cells express the prostate-specific marker, wherein the presence of cancer cells that express the prostate-specific marker is predictive of having prostate cancer in the test subject.

In certain embodiments, the method further comprises determining the amount of the cancer cells that express the prostate-specific marker, wherein such amount is predictive of the stage of prostate cancer in the test subject.

In certain embodiments, the method further comprises determining the expression level of the prostate-specific marker on the cancer cells.

In certain embodiments, the method further comprises grading the cancer cells based on their expression level of the prostate-specific marker, and determining the percentage of the cancer cells in each grade.

In certain embodiments, the method further comprises calculating a grade score for each grade by multiplying the percentage of the cancer cells in that grade with a unique grade number assigned to that grade based on the expression level of the prostate-specific marker, and summing up all the grade scores to obtain an H score, wherein the H score is indicative of the stage of the prostate cancer in the test subject.

In certain embodiments, the cancer cells are identified from the blood sample with a capturing composition comprising a ligand that specifically binds to cancer cells of epithelial origin. In certain embodiments, the ligand is an antibody that specifically binds to an epithelial antigen preferentially expressed on cancer cells. In certain embodiments, the epithelial antigen is Epithelial Cell Adhesion Molecule (EpCAM).

In certain embodiments, the identified cancer cells are enriched in a cell fraction separated from the blood sample. In certain embodiments, the cell fraction is separated under a magnetic field. In certain embodiments, the ligand in the capturing composition is coupled to a magnetic particle.

In certain embodiments, the antibody that specifically binds to a prostate-specific marker comprises an anti-STEAP-1 antibody. In certain embodiments, the anti-STEAP-1 antibody binds to STEAP-1 with a KD of ≤1000 nM. In certain embodiments, the anti-STEAP-1 antibody is a murine monoclonal antibody. In certain embodiments, the anti-STEAP-1 antibody is 15A5, produced by a hybridoma cell having a microorganism deposit number PTA-12259.

In certain embodiments, the cancer cells are identified with one or more reagents that allow detection of cancer cells of epithelial origin. In certain embodiments, the reagents comprise a ligand that specifically binds to a cytokeratin, and wherein the ligand is optionally conjugated with a second detectable label. In certain embodiments, the reagents further comprise a dye that differentiates cells from non-cell components. In certain embodiments, the reagents further comprise a ligand that specifically binds to a leukocyte marker.

In certain embodiments, the cancer cells are detected by a method based on immunofluorescent microscopy, flow cytometry, fiber-optic scanning cytometry, or laser scanning cytometry.

In another aspect, the present disclosure provides methods of predicting efficacy of prostate cancer therapy in a test subject.

In another aspect, the present disclosure provides methods of monitoring response to a prostate cancer therapy in a test subject.

In another aspect, the present disclosure provides antibodies which binds to substantially the same epitope to which antibody 15A5 binds, wherein antibody 15A5 is produced by a hybridoma cell having a microorganism deposit number of PTA-12259.

In another aspect, the present disclosure provides a hybridoma cell line having a microorganism deposit number of PTA-12259.

In another aspect, the present disclosure provides test kits for detecting presence of prostate cancer cells expressing STEAP-1 in a blood sample, comprising an antibody that specifically binds to STEAP-1. In certain embodiments, the test kits further comprises one or more compositions selected from the group consisting of: magnetic particles coupled to a first ligand that specifically binds to cancer cells of epithelial origin, a second ligand that specifically binds to an epithelial marker, a third ligand that specifically binds to a leukocyte marker, and a dye that differentiates cells from non-cell components.

BRIEF DESCRIPTION OF THE FIGURES

(FIG. 2A) expression on LB50 cells; (FIG. 2B) expression on PC3 cells; (FIG. 2C) H score of LB50 cells; and (FIG. 2D) H score of PC3 cells.

(FIG. 3A) expression, (FIG. 3B) H scores.

FIG. 5A, FIG. 5B and FIG. 5C depict H scores of 10 patient blood samples as determined on CellSearch® system using a sheep polyclonal anti-STEAP-1 antibody (FIG. 5A), and the comparison with the IHC results of the tumor tissue samples from the same patients FIG. 5B and FIG. 5C.

FIG. 10 depicts CTC counts of patients during dose escalation treatment from Dose 1-7 pre-dose and post-dose.

DETAILED DESCRIPTION OF THE INVENTION

I. Definitions

Figure 1:
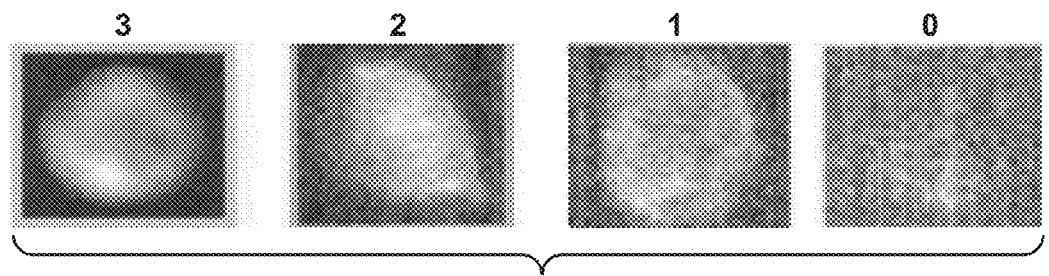
FIG. 1 depicts the representative scoring criteria for CTCs based on the level of staining by an anti-STEAP-1 antibody.

The term "tumor" or "cancer", as used interchangeably herein, refers to any medical condition characterized by neoplastic or malignant cell growth, proliferation, or metastasis, and includes both solid cancers and non-solid cancers such as leukemia.

The term "prostate cancer" or "prostate tumor" as used herein, refers to cancer or tumor that is originated from a prostate tissue.

The term "stage" in the context of a disease (such as cancer or tumor), refers to the progression status of the disease which is indicative of the severity of the disease.

The term "staging" as used herein refers to identifying the particular stage at which the disease has progressed.

The term "diagnosis" (along with grammatical variations thereof such as "diagnosing" or "diagnostic") refers to the identification of a molecular or pathological state, disease or condition, such as the identification of cancer, or refers to the identification of a cancer patient who may benefit from a particular treatment regimen.

The term "prognosis" (and grammatical variations thereof such as "prognosing" or "prognostic") refers to the prediction of the likelihood of benefit from a treatment such as a cancer therapy.

The term "prediction" or "predicting" is used herein to refer to the likelihood that a patient will respond either favorably or unfavorably to a particular anti-prostate cancer therapy. In one embodiment, prediction or predicting relates to the extent of those responses. In one embodiment, the prediction or predicting relates to whether and/or the probability that a patient will survive or improve following treatment, for example treatment with a particular therapeutic agent, and for a certain period of time without disease progression.

The term "benefit" is used in the broadest sense and refers to any desirable effect and specifically includes clinical benefit as defined herein.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term Six-Transmembrane Epithelial Antigen of the Prostate 1, also called STEAP-1, refers to a cell surface antigen predominantly expressed in prostate tissue, and is found to be upregulated in multiple cancer cell lines. Hubert et al. (1999), *Proc. Natl. Acad. Sci. USA*, 96(25), 14523-8. An exemplary human STEAP-1 has an amino acid sequence of SEQ ID NO:1 disclosed in US 2009/0280056 A1, filed 26 Oct. 2007, the entire disclosure of which is expressly incorporated by reference herein.

The terms "anti-STEAP-1 antibody" and "an antibody that binds to STEAP-1" refer to an antibody that is capable of binding STEAP-1 with sufficient affinity such that the antibody is useful as a diagnostic agent in targeting STEAP-1. In one embodiment, the extent of binding of an anti-STEAP-1 antibody to an unrelated, non-STEAP-1 protein is less than about 10% of the binding of the antibody to STEAP-1 as measured, e.g., by a radioimmunoassay (RIA). In certain embodiments, an antibody that binds to STEAP-1 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$M to $10^{-13}$ M, e.g., from $10^{-9}$M to $10^{-13}$ M). In certain embodiments, an anti-STEAP-1 antibody binds to an epitope of STEAP-1 that is conserved among STEAP-1 from different species.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antibody 15A5" as used herein refers to a mouse monoclonal anti-STEAP-1 antibody produced by a hybridoma cell line having a microorganism deposit number of PTA-12259. The microorganism deposit information of the hybridoma cell line is as follows: ATCC Deposit No.: PTA-12259; Deposit Date: Nov. 17, 2011; and Material Deposited: hybridoma 15A5.1.1.1 (also designated 7284), which produces antibody 15A5.

The "class" of an antibody refers to the type of constant domain or constant region possessed by its heavy chain There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The terms "full length antibody," "intact antibody," and "whole antibody" are used herein interchangeably to refer to an antibody having a structure substantially similar to a native antibody structure or having heavy chains that contain an Fc region as defined herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; and toxins such as small molecule toxins or enzymatically active toxins of bacterial, fungal, plant or animal origin, including fragments and/or variants thereof. Non-limiting examples of cytotoxic agents suitable for the present invention include those described in US 2009/0280056 A1, filed 26 Oct. 2007, the entire disclosure of which is expressly incorporated by reference herein. For example, in certain embodiments, a cytotoxic agent is monomethyl auristatin E (MMAE).

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-STEAP-1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "package insert" is used to refer to instructions customarily included in commercial packages of therapeutic products, that contain information about the indications, usage, dosage, administration, combination therapy, contraindications and/or warnings concerning the use of such therapeutic products.

II. Methods

In one aspect, the present disclosure provides methods for diagnosing or staging prostate cancer in a test subject using a blood sample from the test subject. In particular, the present disclosure provides method for diagnosing or staging prostate cancer in a test subject by determining whether the circulating tumor cells (CTCs) express one or more prostate-specific markers.

In the methods provided herein, CTCs are analyzed for expression of one or more prostate specific markers. The detection of prostate specific markers on the CTCs provides further information as to the diagnosis and staging of prostate cancer.

In certain embodiments, the present disclosure provides methods for diagnosing or staging prostate cancer in a test subject, comprising: a) contacting cancer cells of epithelial origin with an antibody that specifically binds to a prostate-specific marker, wherein the cancer cells are from a blood sample taken from the test subject; and b) determining whether any of the cancer cells express the prostate-specific marker, wherein the presence of cancer cells that express the prostate-specific marker is predictive of having prostate cancer in the test subject.

The term "cancer cells of epithelial origin" refers to cancer cells that express at least one epithelial marker. The term "marker" as used herein refers to an antigen molecule that is preferentially expressed on a particular type of cells and helps distinguish those cells from other types of cells. For example, an epithelial marker can be an antigen molecule universally expressed on epithelial cells but not normally found on leukocytes. The cancer cells of epithelial origin may also express a tumor marker, for example, an antigen molecule preferentially found on tumor cells but less frequently found on normal cells. In certain embodiments, the cancer cells of epithelial origin comprise CTCs.

In certain embodiments, the cancer cells of epithelial origin express at least one epithelial marker which is also preferentially found in cancer cells. Detection of such an epithelial marker is indicative of a cancer cell of epithelial origin. In certain embodiments, such an epithelial marker is Epithelial Cell Adhesion Molecule (EpCAM).

The cancer cells of epithelial origin are from a blood sample obtained from the test subject. The blood samples can be any sample that is derived from human blood, for example, a plasma sample, a serum sample, whole blood, or blood that has been treated with certain agents such as an anti-coagulant. Blood samples can be obtained directly from the test subjects, or can be obtained from organizations that collect the samples from the test subjects.

In certain embodiments, the cancer cells are identified from the blood sample with a capturing composition. In certain embodiments, the capturing composition comprises a ligand that specifically binds to cancer cells of epithelial origin. In certain embodiments, the ligand is an antibody that specifically binds to an epithelial antigen preferentially expressed on cancer cells. In certain embodiments, the epithelial antigen is EpCAM.

The term "identify" or "identification" as used herein, refers to substantially differentiating the cancer cells of epithelial origin from the rest of the components in the blood sample. For example, the cancer cells of epithelial origin can be bound or captured by the capturing composition, while the rest of the components are not bound or captured.

The identified cancer cells may or may not be separated from the rest of the components in the blood sample. In certain embodiments, the identified cancer cells are not separated or enriched from the other components in the sample. For example, a blood sample, e.g. a serum sample, may be loaded to a slide, identified with a capturing composition, and without any separation or enrichment operations, the sample may be further contacted with other reagents.

In certain embodiments, the identified cancer cells are enriched in a cell fraction separated from the blood sample. The term "enriched" as used herein refers to the density of the identified cancer cells in the cell fraction is higher than in the blood sample. Any suitable techniques may be used to separate the cell fraction. Techniques commonly employed in the art include, without limitation, gravitational separation, magnetic separation or affinity separation, for example, after the cancer cells form a complex with the capturing composition which allows separation of the cancer cells. For gravitational separation, the capturing composition may be coupled to particles or beads that can be spin down to allow enrichment of the identified cancer cells. For magnetic separation, the capturing composition may be coupled to magnetic particles that can be separated in suitable magnetic fields. For affinity separation, the capturing composition may be immobilized on a device, such as a slide, and allows capture of the identified cells.

In certain embodiments, the cell fraction is separated under a magnetic field. In certain embodiments, the ligand in the capturing composition is coupled to a magnetic particle.

Magnetic particles suitable for the methods disclosed herein can be prepared using methods known in the art, see for example, U.S. Pat. Nos. 5,597,531, 5,698,271, and 6,365,362, and also procedures described in Liberti et al, In Fine Particles Science and Technology, 777-90, E. Pelizzetti (ed.) (1996). Briefly, the magnetic particles comprise a magnetic core (e.g. iron oxides) which is coated with polymers or proteins (e.g., bovine serum albumin and casein). The magnetic mass and size of the magnetic particles can be controlled such that the magnetic particles are magnetically responsive yet are substantially invisible to cell analytical techniques such as immunofluorescence detection. The suitable size of the magnetic particles may be less than 200 nm, preferably with a suitable size distribution range, for example, within 90-150 nm. The magnetic mass of the particles may be between 70-90%.

In certain embodiments, the magnetic particle is colloidal. Such colloidal magnetic particles are substantially stable in solution over an extended period of time, and do not tend to aggregate under gravitational force or in the absence of an applied magnetic field. In certain embodiments, the magnetic particle is colloidal nanoparticles.

The ligand in the capturing composition can be coupled to the magnetic particles using any suitable methods known in the art. For example, the capturing composition may be direct coupled to a magnetic particle using heterobifunctional linkers, such as succinimidylpropiono-dithiopyridine (SPDP), and sulfosuccinimidil-4-[maleimidomethyl]cyclohexane-1-carboxylate (SMCC)). For another example, the capturing composition comprising a biotinylated antibody may be coupled to a magnetic particle conjugated with streptavidin. The capturing composition and the magnetic particles may also be introduced with other conjugating pairs that can bring about the coupling, for example, avidin-biotin, protein A-Antibody Fc, receptor-ligand, and lectin-carbohydrate.

In certain embodiments, the capturing composition comprises an EpCAM antibody coupled to magnetic colloidal nanoparticles. In certain embodiments, the CellSearch® System (Veridex, N.J.) may be used to separate the cell fraction enriched with the identified cells.

The cancer cells of epithelial origin are contacted with an antibody that specifically binds to a prostate-specific marker. The term "prostate-specific" as used herein indicates that, the marker is preferentially found in prostate tissues, and substantially distinguishes prostate tissues or cells from other tissues or cells. In certain embodiments, the prostate-specific marker is a surface or membrane marker of prostate cells. In certain embodiments, the prostate-specific marker is selected from the group consisting of: Six-transmembrane epithelial antigen of the prostate (STEAP-1) (see, e.g. Hubert et al., (1999) *Proc. Natl. Acad. Sci. USA*, 96, 14523-14528), Prostate-specific membrane antigen (PSM) (see, e.g., Israeli, R. S. et al., (1993) *Cancer Res.* 53, 227-230), Prostate carcinoma tumor antigen (PCTA-1) (see, e.g., Su, Z. Z. et al., (1996) *Proc. Natl. Acad. Sci. USA* 93, 7252-7257), and Prostate stem cell antigen (PSCA) (see, e.g., Reiter, R. E. et al. (1998) *Proc. Natl. Acad. Sci USA* 95, 1735-1740). An exemplary human STEAP-1 has an amino acid sequence of SEQ ID NO:1 disclosed in US 2009/0280056 A1, filed 26 Oct. 2007, the entire disclosure of which is expressly incorporated by reference herein.

In certain embodiments, the antibody that specifically binds to a prostate-specific marker comprises an anti-STEAP-1 antibody. In certain embodiments, the anti-STEAP-1 antibody binds to STEAP-1 with a $K_D$ of ≤1000 nM. The anti-STEAP-1 antibody can be a polyclonal antibody or a monoclonal antibody, and can be of any suitable species, such as for example, a sheep antibody, a rabbit antibody, or a murine antibody.

In certain embodiments, the anti-STEAP-1 antibody is a murine monoclonal antibody. In certain embodiments, the anti-STEAP-1 antibody is 15A5, produced by a hybridoma cell having a microorganism deposit number of PTA-12259.

In certain embodiments, the anti-STEAP-1 antibody is an antibody which bind to substantially the same epitope to which antibody 15A5 binds.

In certain embodiments, the anti-STEAP-1 antibody is conjugated with a first detectable label. Any suitable detectable labels may be used. In certain embodiments, the detectable label is a fluorescent label, such as for example, fluorophore AF-488, derivatives of cyanine dyes, fluorescein, rhodamine, Texas red, aminomethylcoumarin (AMCA), phycoerythrin, fluorescein isothiocyanante (FITC), among others. Methods of conjugating an antibody with a detectable label are well known in the art, see for example, Hermanson, G. T., Bioconjugate techniques, Academic Press, 2008.

In certain embodiments, the anti-STEAP-1 antibody is not conjugated. The un-conjugated anti-STEAP-1 antibody can be detected with a secondary antibody conjugated with a detectable label (e.g. the first detectable label). Such secondary antibody can be any antibody raised in a different species than the anti-STEAP-1 antibody and recognizes the constant region of the anti-STEAP-1 antibody, as is commonly employed in the art.

In certain embodiments, the cancer cells are identified with one or more reagents that allow detection of cancer cells of epithelial origin.

In certain embodiments, the reagents comprise a ligand that specifically binds to an epithelial marker. In certain embodiments, the epithelial marker is not EpCAM. In certain embodiments, the epithelial marker is a cytokeratin. Cytokeratins are a group of proteins typically expressed in epithelial cells, and form keratin-containing filaments in the cytoskeleton of epithelial tissue.

In certain embodiments, the ligand that specifically binds to an epithelial marker is an anti-cytokeratin antibody, optionally conjugated with a second detectable label. Any suitable detectable label may be used, for example, a fluorescent label such as phycoerythrin.

In certain embodiments, the reagents further comprise a cell-specific dye that differentiates cells from non-cell components. For example, dyes that stain cell nucleus may be used. In certain embodiments, the dye is 4',6-diamidino-2-phenylindole (DAPI).

In certain embodiments, the reagents further comprise a ligand that specifically binds to a leukocyte marker. The leukocyte marker may be selected as universally expressed on leukocytes but not typically on non-leukocytes, for example, CD45 may be a suitable leukocyte marker. In certain embodiments, the ligand that specifically binds to a leukocyte marker is conjugated with a third detectable label. For example, the ligand can be an anti-CD45 antibody conjugated with allophycocyanin. The staining of the identified cells by an anti-CD45 antibody can be helpful to exclude the leukocytes from the CTCs of epithelial origin.

In case more than one detectable label (including a dye) is used in one testing, it is preferred that the detectable labels are selected such that each label can be independently detected without substantial interference to any other detectable signals present in the sample. For example, the detectable labels (including a dye) may be different fluorescent molecules showing different colors under the detection condition.

The detection can be carried out by any suitable method, for example, those based on immunofluorescent microscopy, flow cytometry, fiber-optic scanning cytometry, or laser scanning cytometry.

In certain embodiments, the cancer cells are visualized under fluorescent microscopy after stained with cell-specific dye and differently labeled antibodies or ligands for epithelial marker, prostate-specific marker and leukocyte marker. The cells positive for cell-specific dye, epithelial marker and prostate-specific marker, but negative for leukocyte marker are classified as cancer cells of epithelial origin that express the prostate-specific marker. Such cells may also be analyzed using flow cytometry, see, for example, Cruz, I., et al., *Am J Clin Pathol*, Vol. 123: 66-74 (2005).

Alternatively, the cancer cells may also be deposited on a surface of a glass slide, and scanned for cells positive for cell-specific dye, epithelial marker and prostate-specific marker, but negative for leukocyte marker (see, for example, Marrinucci, D. et al., *Human Pathology*, Vol. 38, No. 3, 514-519 (2007)). Similarly, the identified cells deposited on a glass slide may also be analyzed using laser-scanning technology (see, for example, Pachmann, K. et al., *Breast Cancer Research*, Vol. 7, No. 6, R975-R979 (2005)).

In certain embodiments, the methods further comprise determining the amount of the cancer cells that express the prostate-specific marker, wherein such amount is predictive of the stage of prostate cancer in the test subject. Assumptions have been made to correlate the size and/or aggressiveness of a tumor with the number of tumor cells in peripheral blood. For example, it is reported that a patient with a 1-mm diameter tumor may have a frequency of tumor cells in peripheral blood of about 6 tumor cells per 100 ml blood (see, for example, U.S. Pat. No. 6,365,362). Assuming an increase in tumor size may be proportional to this frequency, criteria may be established to indicate the stage of the cancer in the test subject. In certain embodiments, clinical blood samples from patients diagnosed of early stage or metastatic prostate cancer may be used to determine a statistical level of cancer cells in the peripheral blood for those patients, and thereby provides for criteria for future detection and analysis.

In certain embodiments, the methods further comprise determining the expression level of the prostate-specific marker on the cancer cells. Some prostate-specific markers are antigens whose expression level may be up-regulated as a result of tumor growth, metastasis and/or an advanced stage of the cancer. Such prostate-specific markers may include, without limitation, STEAP-1, PSMA, PCTA-1, and PSCA. The expression levels of the prostate-specific markers on the cancer cells may be determined by any suitable methods, for example, by determining the intensity of the fluorescence signal corresponding to the prostate-specific marker.

In certain embodiments, the methods further comprise grading the cancer cells based on their expression level of the prostate-specific marker, and determining the percentage of the cancer cells in each grade. In certain embodiments, cancer cells expressing high level, medium level and low level of the prostate-specific marker are respectively graded. The criteria for "high level", "medium level", and "low level" can be determined, for example, using established cell lines having known expression levels of the marker. For example, the LB50 cell line is known to express a high level of STEAP-1, the LnCAPner cell line is known to express a medium level of STEAP-1, and the PC3 cell line is known to express a low level of STEAP-1. Therefore, cancer cells as detected to have a STEAP-1 expression level comparable to or higher than the LB 50 cell line may be graded as "high level". Similarly, "medium level" may be assigned to cancer cells whose STEAP-1 expression level is comparable to or higher than that of LnCAPner cell line but is lower than that of LB 50 cell line. Those having an STEAP-1 expression level comparable to or lower than that of PC3 cell line may be graded as or "low level."

The number of the cancer cells in each grade may be further determined. In certain embodiments, the percentage of the cancer cells in each grade may be calculated. A higher percentage of cancer cells in the high level grade can be indicative of a more advanced stage of the prostate cancer. Similarly, prostate cancer at an early stage may show lower percentage of cancer cells in the high level grade, and/or higher percentage of cancer cells in low level grade.

In certain embodiments, the methods further comprise calculating a grade score for each grade by multiplying the percentage of the cancer cells in that grade with a unique grade number assigned to that grade based on the expression level of the prostate-specific marker, and summing up all the grade scores to obtain an H score, wherein the H score is indicative of the stage of the prostate cancer in the test subject. For example, a grade number of 3 may be assigned to the high level grade, 2 to the medium level grade, and 1 to the low level grade, which defines the range of the H score within 0 to 300. A higher H score is indicative of more cells in the high level grade, i.e. a more advanced stage of the prostate cancer, and a lower H score indicates more cells in the low level grade, i.e. a relatively early stage of the prostate cancer.

In some embodiments, the methods further comprise determining the presence of a marker and/or frequency of presence of a marker. In some embodiments, the presence of a marker is determined by immunohistochemical ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Northern analysis, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. In some embodiments, the presence of a marker is determined by fluorescent in situ hybridization (FISH). In some embodiments, the marker is PTEN. In some embodiments, the CTC is triploid. In some embodiments, the CTC is triploid with PTEN loss. In some embodiments, the CTC is determined to be triploid by CEP10 FISH. In some embodiments, the CTC is determined comprise PTEN loss by PTEN FISH.

In another aspect, the present disclosure also provides methods of predicting efficacy of prostate cancer therapy in a test subject, comprising: a) contacting cancer cells of epithelial origin with an antibody that specifically binds to a prostate-specific marker, wherein the cancer cells are from a blood sample taken from the test subject; and b) determining whether any of the cancer cells express the prostate-specific marker, wherein the presence of cancer cells that express the prostate-specific marker is predictive of the efficacy of the prostate cancer therapy in the test subject.

Certain prostate-specific markers may also be therapeutic targets for prostate cancer treatment. Therefore, the expression level of such marker on the CTCs and changes in such level can be predicative of the efficacy of therapies that target such marker.

In certain embodiments, the methods further comprise determining the amount of the cancer cells that express the prostate-specific marker, and/or determining the expression level of a prostate-specific marker on the cancer cells. For example, the expression level of a prostate-specific marker (e.g. STEAP-1) on the cancer cells from the baseline pre-treated sample in early phase clinical trials can be correlated with clinical endpoints such as progression free survival, PSA changes, patient-reported bone pain, overall survival, or others, in order to determine whether expression of the prostate-specific marker above a certain threshold is predictive of clinical activity of the prostate cancer therapy (e.g. STEAP-1 Antibody-Drug Conjugate (ADC) based therapy). Dynamic changes in expression level of the prostate-specific marker (e.g. STEAP-1) in the cancer cells (i.e. down-regulation in post-treatment samples) can also be correlated to clinical outcome measures to determine if such changes are predictive of therapeutic activity. Such methods can be used as a first step in qualifying the assay as a candidate predictive biomarker that could be used to select patients for a prostate cancer therapy (e.g. STEAP-1 ADC-based therapy), followed by prospective validation in a confirmatory phase III study.

In another aspect, the present disclosure also provides methods of monitoring response to a prostate cancer therapy in a test subject, comprising: a) contacting a first group of cancer cells of epithelial origin with an antibody that specifically binds to a prostate-specific marker, wherein the first group of cancer cells are from a first blood sample taken from the test subject; b) determining the amount of the cancer cells in the first group that express prostate-specific marker and/or the expression level of the prostate-specific marker in the cancer cells; c) contacting a second group of cancer cells of epithelial origin with the antibody that specifically binds to a prostate-specific marker, wherein the second group of cancer cells are from a second blood sample taken from the test subject after a test period of prostate cancer therapy; d) determining the amount of the cancer cells in the second group that express prostate-specific marker and/or the expression level of the prostate-specific marker in the cancer cells; and e) comparing the amount of the cancer cells that express the prostate-specific marker and/or the prostate-specific marker expression level as determined in b) with that in step d), wherein the change in the amount of the cancer cells expressing the prostate-specific marker and/or an increase in the prostate-specific marker expression level in the cancer cells is predicative of the response to the prostate cancer therapy in the test subject. In certain embodiments, the prostate-specific marker is STEAP-1.

III. Antibodies

In another aspect, the present disclosure provides antibodies which bind to substantially the same epitope to which antibody 15A5 binds, wherein antibody 15A5 is produced by a hybridoma cell having a microorganism deposit number of PTA-12259.

In certain embodiments, the antibodies provided herein compete with 15A5 antibody for binding to STEAP-1. Competition assays may be used to identify an antibody that competes with the anti-STEAP-1 antibody 15A5 for binding to STEAP-1.

In an exemplary competition assay, immobilized STEAP-1 is incubated in a solution comprising a first labeled antibody that binds to STEAP-1 (e.g., 15A5) and a second unlabeled antibody that is being tested for its ability to compete with the first antibody for binding to STEAP-1. The second antibody may be present in a hybridoma supernatant. As a control, immobilized STEAP-1 is incubated in a solution comprising the first labeled antibody but not the second unlabeled antibody. After incubation under conditions permissive for binding of the first antibody to STEAP-1, excess unbound antibody is removed, and the amount of label associated with immobilized STEAP-1 is measured. If the amount of label associated with immobilized STEAP-1 is substantially reduced in the test sample relative to the control sample, then that indicates that the second antibody is competing with the first antibody for binding to STEAP-1. See Harlow and Lane (1988) *Antibodies: A Laboratory Manual* ch. 14 (Cold Spring Harbor Laboratory, Cold Spring Harbor, N.Y.).

In certain embodiments, the antibodies provided herein has a dissociation constant (Kd) to STEAP-1 of ≤1000 nM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$ M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25

μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Kinetic binding measurements can also be performed on an Octet Red instrument (ForteBio, Menlo Park, Calif., USA). For example, all washes, dilutions and measurements are performed in Octet buffer (0.2% dodecylmaltoside, or DDM, –PBS) with the plate shaking at 1000 rpm. Streptavidin biosensors are equilibrated in Octet buffer for 10 min and then loaded with biotinylated STEAP-1 (from viral lysate in 1% DDM, diluted 1:8 in Octet Buffer) for 5 min and washed for 10 min. For the association phase, the ligand-coated streptavidin tips are immersed in anti-STEAP-1 antibody fragments for 10 min (eight serial two-fold dilutions, starting at 500 or 50 nM). Dissociation of the Ab-STEAP-1 complex can be measured in wells containing Octet buffer alone for 600 s. KD, Ka and Kd are determined with Octet evaluation software v6.3 using a 1:1 binding model with global fitting.

In certain embodiments, the antibodies provided herein include, without limitation, murine antibodies, sheep antibodies and rabbit antibodies. In certain embodiments, the antibodies are murine monoclonal antibody.

In certain embodiments, the antibodies provided herein comprise at least one of the CDR regions of the antibody 15A5. The CDR regions of an antibody can be determined using methods known in the art. Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in heavy chain variable regions, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, CDR residues and other residues in the variable domain (e.g., FR residues) are numbered herein according to Kabat et al., supra.

In certain embodiments, the antibodies provided herein comprise at least one of the heavy chain variable regions of the antibody 15A5, or at least one of the light chain variable regions of the antibody 15A5.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

Antibody fragments of the antibodies provided herein are also encompassed by the present disclosure. In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

In certain embodiments, the antibodies provided herein is antibody 15A5 or its antigen binding fragment.

In certain embodiments, the antibodies provided herein are further conjugated with a detectable label. Suitable labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^3H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

IV. Nucleic Acids and Host Cells

Antibodies may be produced using recombinant methods and compositions, e.g., as described in U.S. Pat. No. 4,816, 567. In one embodiment, isolated nucleic acid encoding an anti-STEAP-1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-STEAP-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-STEAP-1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

A hybridoma cell line is also provided herein, having a microorganism deposit number of PTA-12259. The hybridoma cell line produces the antibody 15A5.

V. Use of the Antibodies

The antibodies provided herein can be used in the manufacture of a diagnostic reagent for prostate cancer. The antibodies may be further conjugated with a detectable label suitable for the diagnostic purpose, and may be presented in a suitable form, such as in lyophilized powers or in suitable solution form.

VI. Test Kits

In another aspect of the present disclosure, test kits containing compositions useful for the diagnosis or prognosis of prostate cancer is provided.

The present disclosure further provides test kits for detecting presence of prostate cancer cells expressing STEAP-1 in a blood sample, comprising an antibody that specifically binds to STEAP-1.

In certain embodiments, the antibody is conjugated with a first detectable label. Any suitable detectable label may be used, such as fluorescent label.

In certain embodiments, the antibody is an anti-STEAP-1 antibody provided herein. In certain embodiments, the antibody is antibody 15A5.

In certain embodiments, the test kits further comprise one or more compositions selected from the group consisting of: magnetic particles coupled to a first ligand that specifically binds to cancer cells of epithelial origin, a second ligand that specifically binds to an epithelial marker; a third ligand specifically binds to a leukocyte marker, and a dye that differentiates cells from non-cell components.

In certain embodiments, the second ligand is conjugated to a second detectable label, and/or the third ligand is conjugated to a third detectable label. In certain embodiments, when the test kits comprises more than one detectable label (including a dye), it is preferred that the detectable labels (including a dye) are selected such that each label can be independently detected without substantial interference to any other detectable signals present in the sample.

In certain embodiments, the first ligand, the second ligand and/or the third ligand comprises an antibody. In certain embodiments, the first ligand comprises an anti-EpCAM antibody. In certain embodiments, the second ligand comprises an anti-keratin antibody. In certain embodiments, the third ligand comprises an anti-CD45 antibody.

The test kits can further comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for diagnosing the condition. At least one reagent in the composition is an antibody of the invention. The label or package insert indicates that the composition is used for in vitro diagnosis of the condition of choice.

VII. Examples

The following are examples of methods and compositions of the invention. It is understood that various other embodiments may be practiced, given the general description provided above.

Example 1. Detection of STEAP-1 on Different Cell Lines

Three anti-STEAP-1 antibodies were used to detect STEAP-1 expression on three prostate cancer cell lines using an immunohistochemistry (IHC) assay. 293 LB50 was used as a high STEAP-1 expressing cell line; LnCAPner was used as a medium STEAP-1 expressing cell line; and PC3 was used as a low to negative STEAP-1 expressing cell line. The tested anti-STEAP-1 antibodies were: antibody-37, which is a mouse monoclonal anti-STEAP-1 antibody; a sheep polyclonal anti-STEAP-1 antibody, and sc-25514, which is a rabbit polyclonal anti-STEAP-1 antibody. The three antibodies were conjugated with the fluorophore AF-488.

The antibodies were incubated respectively with the three cell lines. Antibody-antigen bindings were visualized under fluorescent microscopy for AF-488 signal. Results showed that all three antibodies gave expected signal intensities relative to the expression levels of the three cell lines, i.e., the antibodies showed strongest staining on 293 LB50 cells, medium staining on LnCAPner cells, and low to negative staining on PC3 cells.

Example 2. Detection of STEAP-1 Expression in Prostate Cancer Cells Using Anti-STEAP-1 Antibodies on the CellSearch® System The three antibodies (mouse antibody-37, Sheep polyclonal antibody, and rabbit sc-25514) were tested on the CellSearch® system for their ability to detect the STEAP-1 expression on LB50 cells and PC3 cells, respectively.

The spike-in assay was performed as follows. The LB50 cells and PC3 cells were grown in T75 flasks. When cells reached 80% confluence, cells were washed with 10 ml PBS and then treated with 3 ml trypsin. 7 ml of media was added to the detached cells, and the whole suspension was transferred into a falcon tube followed by centrifugation for 5 minutes at 13000 rpm. Supernatant was removed and the pellet was re-suspended in 10 ml of PBS. 0.5 ml of each cell suspension was transfer into vicell tubes and counted using the Beckman Coulter counter. The cell suspension was diluted to 5000 cells/ml solution in 10 ml of media. A suitable amount of cells were spiked into 10 ml blood, in which 7.5 ml of blood was to be used in the CellSearch method. For 100 cell spike in, 26.6 uls of the cell suspension was added to 10 ml of blood. The blood with cells spiked-in was rotated for 20 minutes.

To ensure there were approximately 100 cells spiked into blood, 5 ul of each cell suspension was added onto poly L lysine gridded slides (electron microscopy science) repetitively for 5 times. 5 ul cell suspension approximately equaled to 25 cells. The cells on each slide were counted, and the cell number was used to calculate the recovery of the cells by counting the number of "CTCs" (i.e., spiked-in cells) captured on CellSearch/the actual number of cells counted on slide.

When the blood with cells spiked-in has been thoroughly mixed, the blood samples were run on CellSearch with the three anti-STEAP-1 antibodies, respectively, following the CellSearch CTC protocol. Briefly, each testing sample was mixed with anti-EpCAM antibody conjugated with magnetic colloid nanoparticles, and then was subject to a magnetic field to allow separation of a cell fraction enriched with EpCAM positive epithelial cells in the sample. The cell fraction was then mixed with phycoerythrin-conjugated anti-cytokeratin antibodies, allophycocyanin-conjugated anti-CD45 antibodies, DAPI, and one of the three anti-STEAP-1 antibodies conjugated with AF-488, which was used in the 4th filter. The conjugated anti-STEAP-1 antibodies were diluted to 1:50 in PBS. The samples were run on CellSearch and the CTCs were scored on the CellTracks analyzer. Cells stained positive for cytokeratin and DAPI, but negative for CD45 were determined as CTCs. CTCs on the CellSearch autoprep systems that showed STEAP-1 staining were selected, and were further quantified for fluorescence intensities of the anti-STEAP-1 antibody that indicated the STEAP-1 expression level.

CTCs with STEAP-1 expression were scored based on the staining intensity, i.e. the level of expression of STEAP-1. CTCs with high STEAP-1 expression, which was demonstrated by strong staining intensity and minimal to no background was given a score of 3, medium staining intensity with some background was given a score as 2 and low staining intensity with relatively high background was given a score of 1. A representative example is shown in FIG. 1.

Figure 2A:
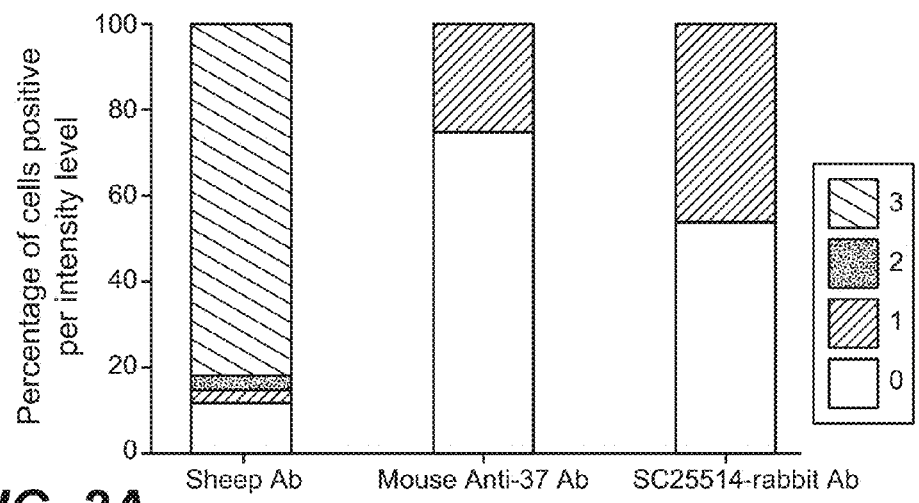
FIG. 2A, FIG. 2B, FIG. 2C and FIG. 2D depict the STEAP-1 expression and H scores of different cell lines as determined on CellSearch® system using a sheep polyclonal anti-STEAP-1 antibody, a mouse monoclonal anti-STEAP-1 antibody 37, and a rabbit polyclonal anti-STEAP-1 antibody.
Figure 2B:
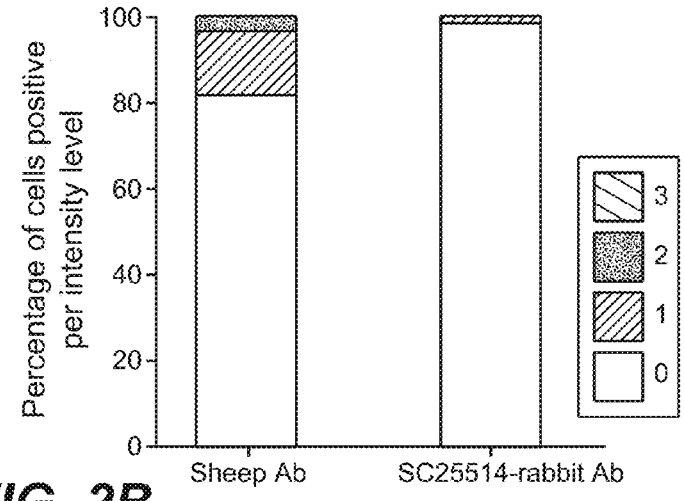

As shown in FIG. 2A, all three tested antibodies detected the STEAP-1 high expresser LB50 cells spiked in to the blood, although the dynamic range was different. As shown in FIG. 2B, the sheep polyclonal antibody and the rabbit sc-25514 also detected STEAP-1 low expresser PC3 cells spiked in to the blood.

H score was calculated for the CTCs with STEAP-1 expression, from the sum of (1×the percentage of cells staining weakly positive)+(2×the percentage of cells staining moderately positive)+(3×the percentage of cells staining strongly positive) with a maximum score of 300 (McCall et al. (2008) *British Journal of Cancer* 98(6): 1094-1101).

Figure 2C:
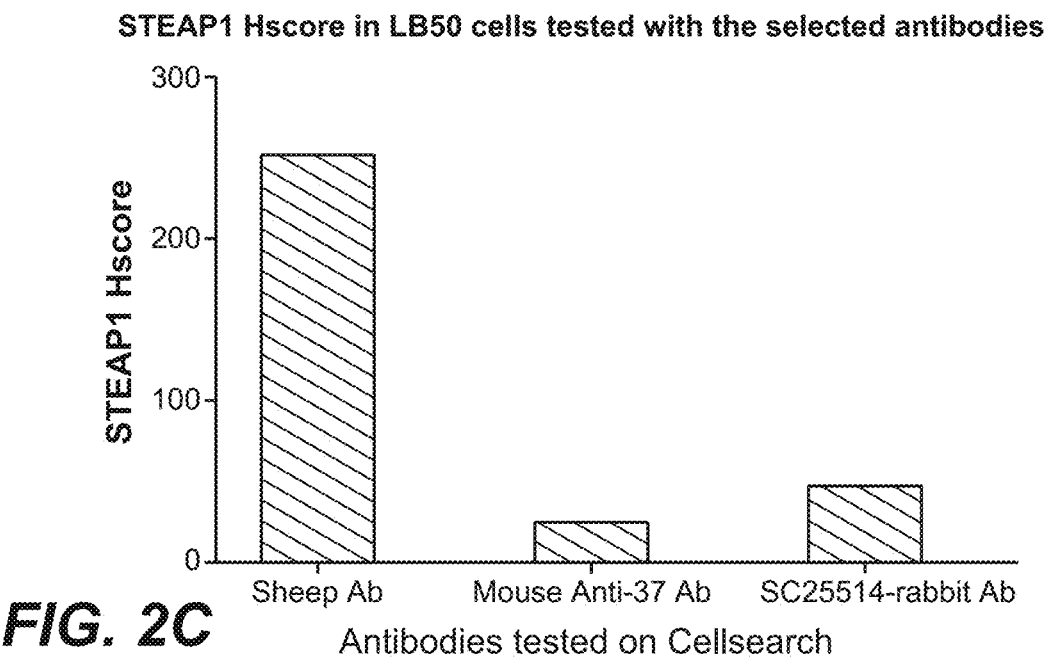
Figure 2D:
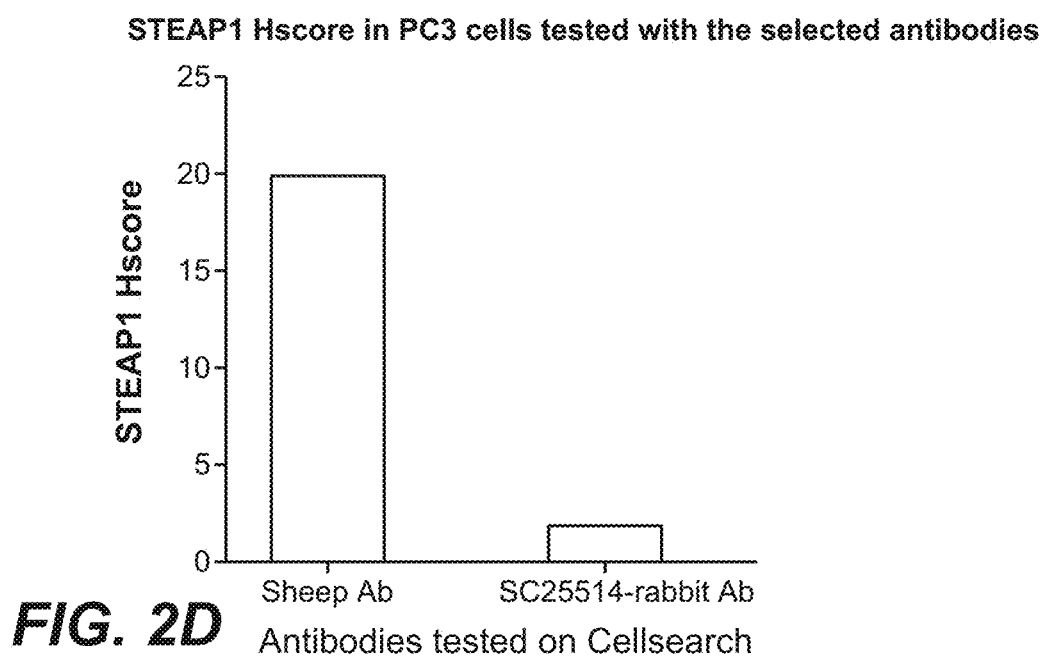

As shown in FIG. 2C and FIG. 2D, sheep polyclonal antibody demonstrated the best dynamic range, and therefore sheep polyclonal antibody was chosen for further testing with clinical samples.

Example 3. Analysis of STEAP-1-Expressing Cells in Spiked-in Samples Using Sheep Polyclonal Antibody on the CellSearch® System The anti-STEAP-1 sheep polyclonal antibody was used to determine STEAP-1 expression on cells spiked-in to blood samples. The spike-in assay was performed in a similar procedure as described in Example 2. The three cell lines, 293 LB50, LnCAPner and PC3 were spiked in to respective blood samples and mixed thoroughly. The sheep polyclonal antibody was diluted to 1:50 in PBS and added to the blood sample in the $4^{th}$ filter on CellSearch. The samples were run on CellSearch and the CTCs were scored on the CellTracks analyzer. Cells stained positive for cytokeratin and DAPI, but negative for CD45 were determined as CTCs. CTCs on the CellSearch autoprep systems that showed STEAP-1 staining were selected, and were further quantified for fluorescence intensities of the anti-STEAP-1 antibody that indicated the STEAP-1 expression level. H scores were also calculated according the same method as described in Example 2.

Figure 3A:
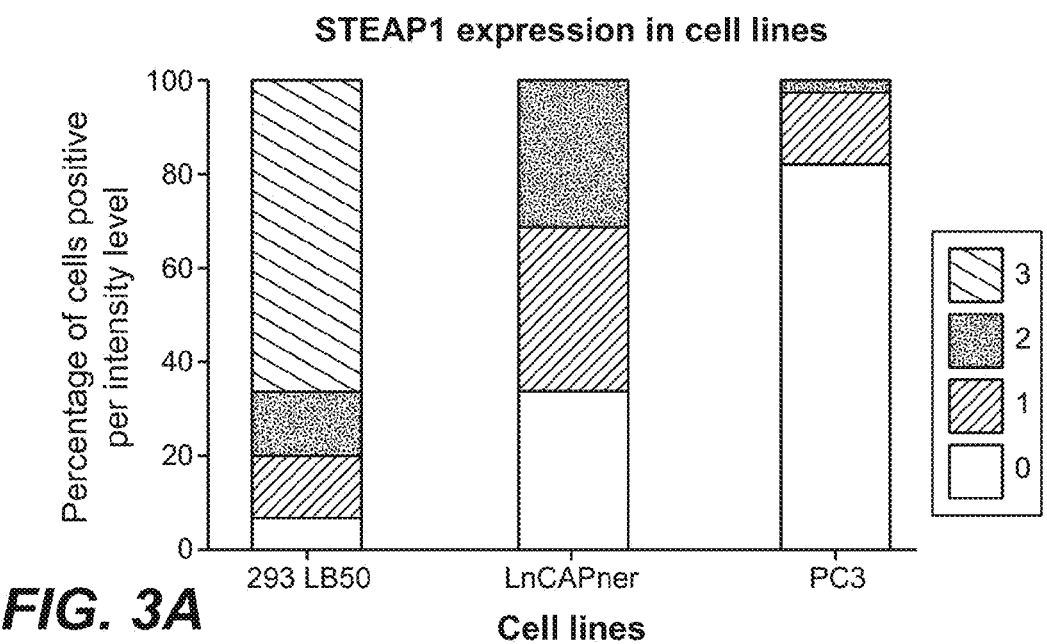
FIG. 3A and FIG. 3B depict the STEAP-1 expression and H scores of different spiked-in samples as determined on CellSearch® system using a sheep polyclonal anti-STEAP-1 antibody.
Figure 3B:
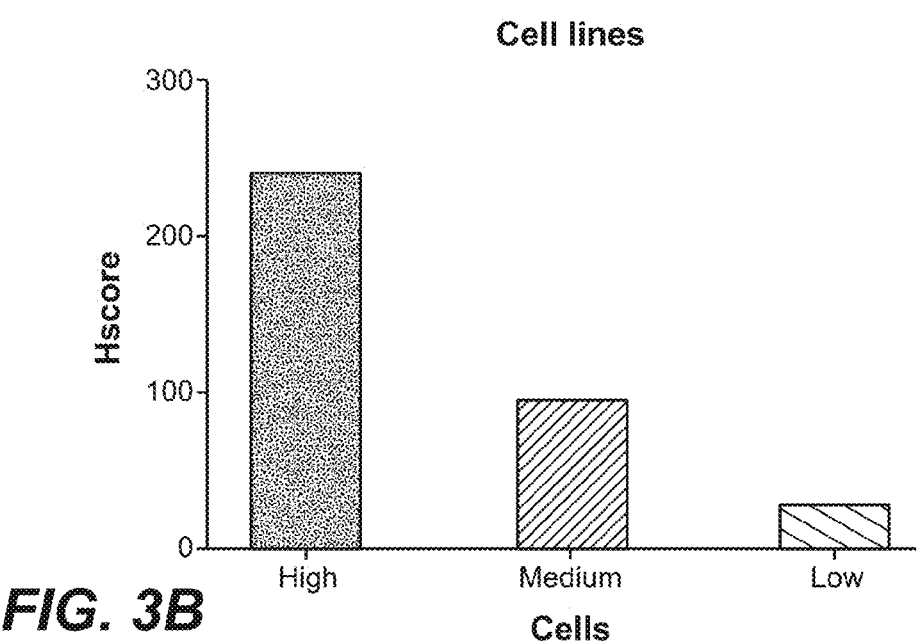

As shown in FIG. 3A and FIG. 3B, the sheep polyclonal antibody detected STEAP-1 expression on all of the three cell lines tested and with good dynamic range. As detected by the sheep polyclonal antibody, the sample spiked in with 293 LB50 cells had the more than 60% CTCs with a high intensity level, and the H score was determined above 200; the sample spiked in with LnCAPner cells had an H score of about 100; and the sample spiked in with PC3 cells had an H score of below 100.

Figure 4:
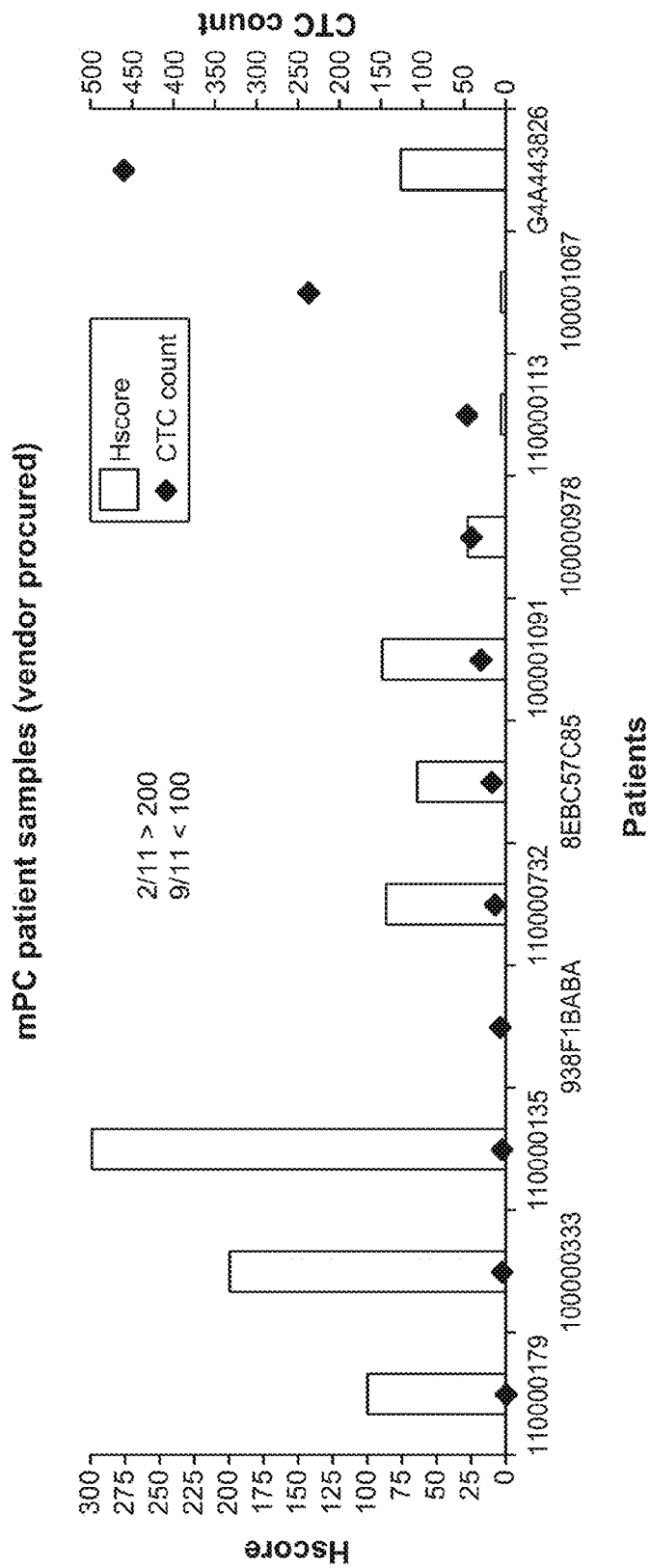
FIG. 4 depicts the H scores of 11 patient blood samples as determined on CellSearch® system using a sheep polyclonal anti-STEAP-1 antibody.

Example 4. Detection of STEAP-1 Expression in CTCs of Prostate Cancer Patients Using Anti-STEAP-1 Antibody on the CellSearch® System Blood samples from 11 prostate cancer patients were obtained from a clinic. The blood samples were analyzed on the CellSearch® system using the anti-STEAP-1 sheep polyclonal antibody. The sheep polyclonal antibody was diluted to 1:50 in PBS and added to the blood sample in the $4^{th}$ filter on CellSearch. The samples were run on CellSearch and the CTCs were scored on the CellTracks analyzer. Cells stained positive for cytokeratin and DAPI, but negative for CD45 were determined as CTCs. CTCs on the CellSearch autoprep systems that showed STEAP-1 staining were selected, and were further quantified for fluorescence intensities of the anti-STEAP-1 antibody that indicated the STEAP-1 expression level. The number of CTCs were counted for each sample, and H scores were also calculated as described in Example 2. Results are shown in FIG. 4.

Example 5. Correlation of CTC Assay with Immunohistochemistry (IHC) Assay

Blood samples and tumor tissue samples were collected from 10 prostate cancer patients in a phase I clinical trial.

The blood samples were analyzed on the CellSearch® system using the anti-STEAP-1 sheep polyclonal antibody. The number of CTCs was counted for each sample, and H scores were also calculated as described in Example 2. Results are shown in FIG. 5A.

The tumor tissue samples were tested using conventional IHC methods, and the expression level of STEAP-1 in the tissue were shown in overall scores: 1+, 2+ and 3+. The larger number indicated the higher expression level of STEAP-1.

Figures 5A, 5B:
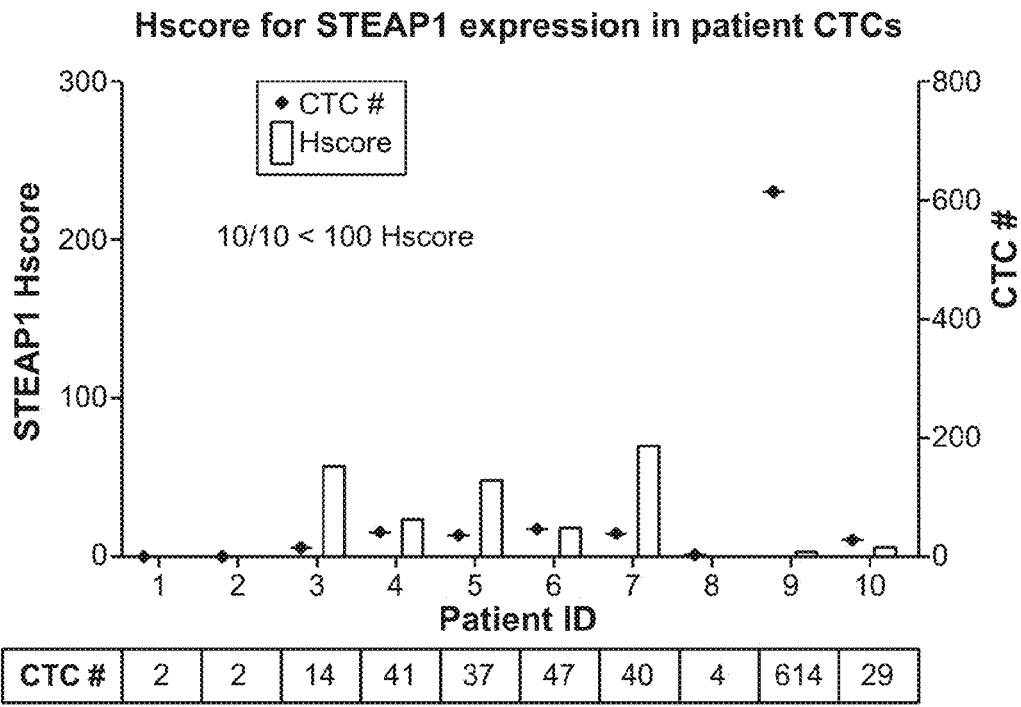
Figure 6A:
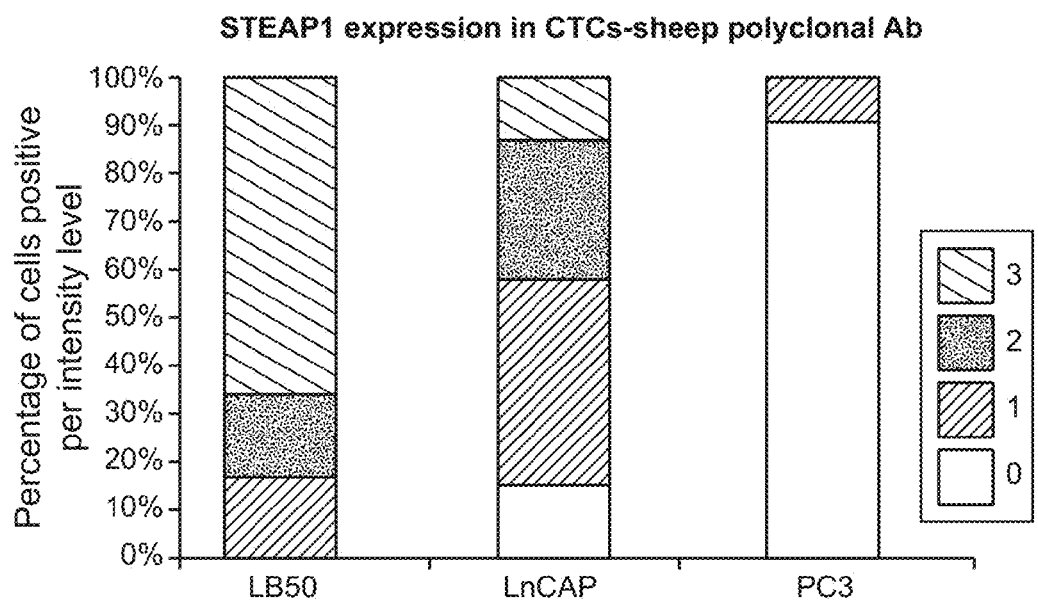
FIG. 6A, FIG. 6B, FIG. 6C and FIG. 6D depict the STEAP-1 expression and H scores of different spiked-in samples as determined on CellSearch® system using a sheep polyclonal anti-STEAP-1 antibody (FIG. 6A and FIG. 6B) and the mouse monoclonal anti-STEAP-1 antibody 15A5 (FIG. 6C and FIG. 6D).
Figure 6B:
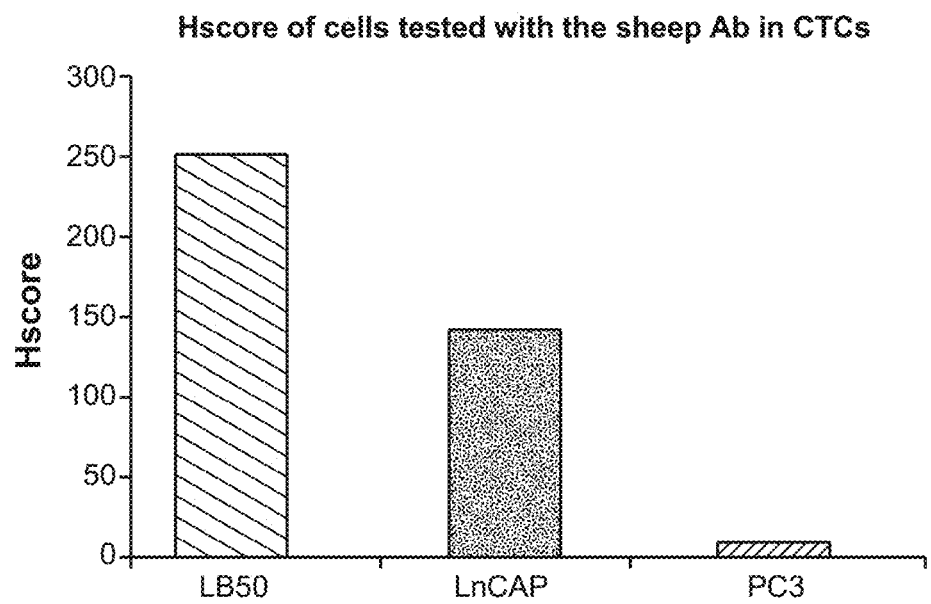
Figure 6C:
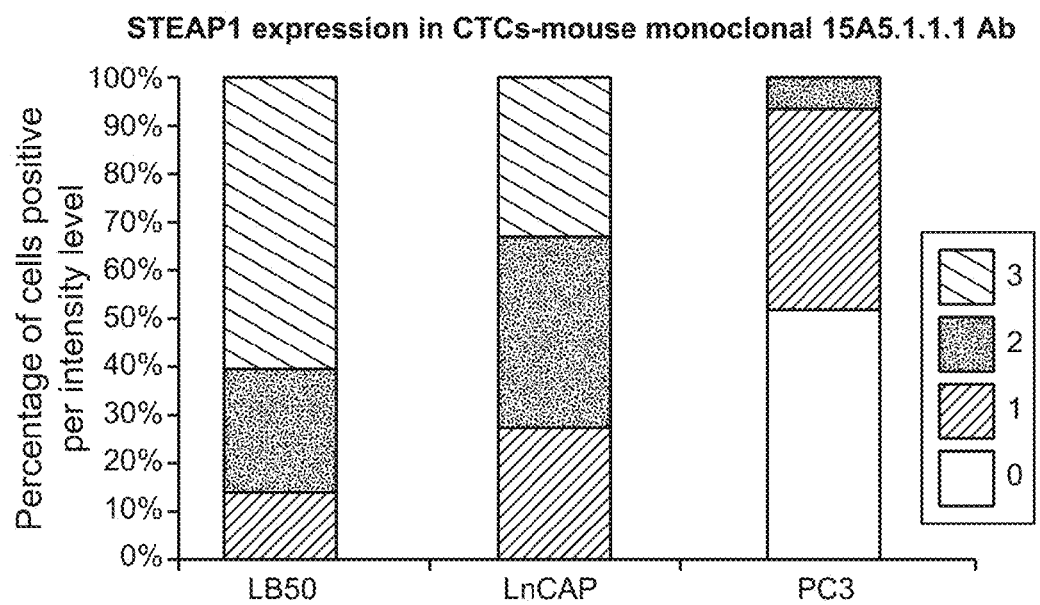
Figure 6D:
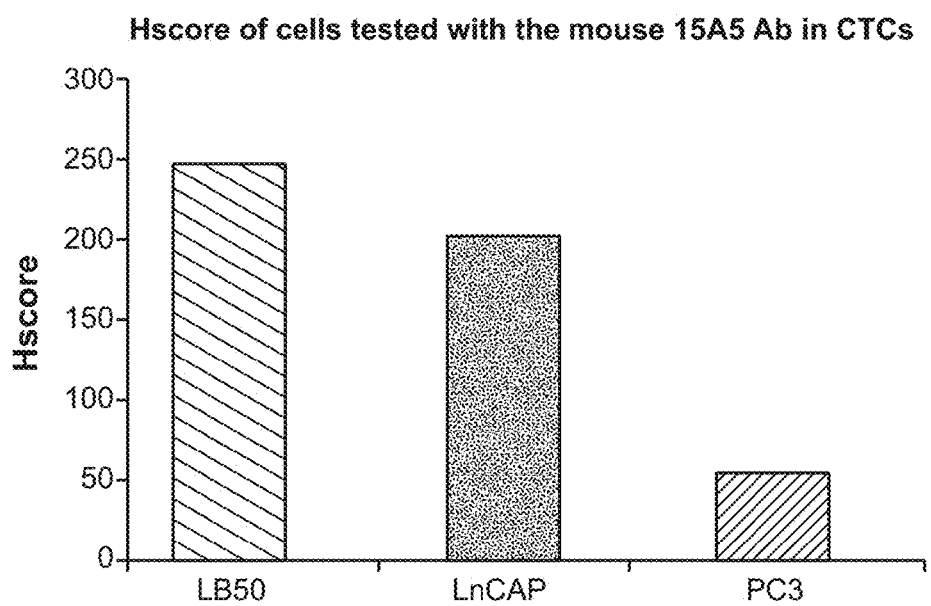

The CellSearch® results and the IHC results are shown and compared in FIG. 5B and FIG. 5C. The CellSearch® results showed good correlation with the IHC results, indicating that the CellSearch® method using the sheep polyclonal antibody was effective in detecting the STEAP-1-expressing CTCs in blood sample.

Example 6. Comparison of the Sheep Polyclonal Antibody with the Mouse Monoclonal Antibody 15A5

The mouse monoclonal antibody 15A5 was tested using the spike-in assay on the CellSearch® system and compared with the sheep polycolncal antibody. 293 LB50 cells (high-expresser), LnCAPner cells (medium-expresser), and PC3 cells (low-expresser) were spiked into respective blood samples as described in Example 2. The blood samples were analyzed on the CellSearch® system, using the sheep polyclonal antibody and the mouse monoclonal antibody 15A5, respectively. H scores were also calculated. The procedure and methods were similar to those described in Example 2.

As shown in FIG. 6A, FIG. 6B, FIG. 6C and FIG. 6D, both antibodies showed comparable results for each sample in intensity level and in H score. The mouse monoclonal antibody 15A5 also showed good dynamic range in the assay.

There are advantages to using monoclonal antibody 15A5 over a polyclonal antibody. For example, the monoclonal antibody will show less batch-to-batch variability, less background, and greater reproducibility among experiments, as compared to a polyclonal antibody.

Example 7. Analysis of STEAP-1-Expressing Cells in Patient Samples Using the Mouse Monoclonal Antibody 15A5 on the CellSearch® System Blood samples from prostate cancer patients are collected and analyzed on the CellSearch® system using the anti-STEAP-1 monoclonal antibody 15A5. The antibody 15A5 is diluted to, for example, 1:50 in PBS and added to the blood sample. The samples are run on CellSearch and the CTCs scored on the CellTracks analyzer. Cells stained positive for cytokeratin and DAPI, but negative for CD45 are determined as CTCs. CTCs on the CellSearch autoprep systems that show STEAP-1 staining are selected and further quantified for fluorescence intensities of the anti-STEAP-1 antibody that represent the STEAP-1 expression level. The number of CTCs are counted for each sample, and H scores are also calculated as described in Example 2.

Furthermore, the expression level of STEAP-1 on CTCs in blood samples collected from "baseline" (i.e., pre-treated) patients in clinical trials are correlated with clinical endpoints such as progression free survival, PSA changes, patient-reported bone pain, overall survival, or others, in order to determine whether expression of the prostate-specific marker above a certain threshold is predictive of clinical activity of the prostate cancer therapy (e.g., an anti-STEAP-1 Antibody-Drug Conjugate (ADC) based therapy). Dynamic changes in expression level of the prostate-specific marker (e.g. STEAP-1) in the cancer cells (i.e., down-regulation in post-treatment samples) is correlated to clinical outcome measures to determine if such changes are predictive of therapeutic activity. Such methods can be used as a first step in qualifying the assay as a candidate predictive biomarker that could be used to select patients for a prostate cancer therapy (e.g. anti-STEAP-1 ADC-based therapy), followed by prospective validation in a confirmatory phase III study.

Example 8. CTC Enumeration in Patient Samples

Figure 7A:
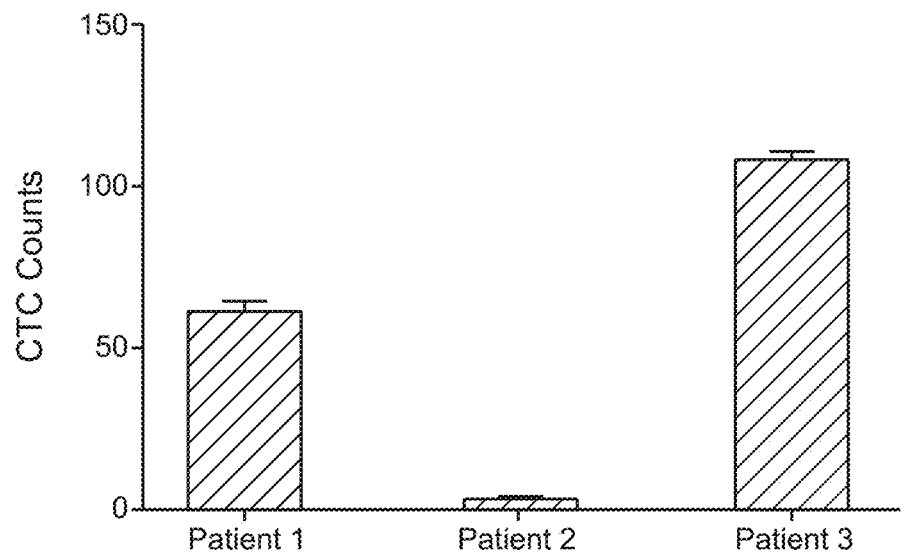
FIG. 7A and FIG. 7B depict reproducibility of CTC enumeration in duplicate patient samples as shown by CTC counts/patient (FIG. 7A) and reproducibility of STEAP1 biomarker expression levels in CTCs from duplicate patient samples as shown by H-score/patient (FIG. 7B).

Blood samples from prostate cancer patients were drawn in duplicate before initiation of therapy (Baseline samples). Samples were analyzed on the CellSearch® system and CTC enumeration was scored on the CellTracks analyzer as described above. Briefly, cells stained positive for cytokeratin and DAPI, but negative for CD45 were scored as CTCs. Mean CTC counts and STDEV were computed for each duplicate pair, and errors (+−SDEV) were plotted in a histogram. As shown in FIG. 7A, there was a large dynamic range for mean CTC enumeration in these patients, with tight counts between duplicate samples (small error bars), demonstrating high reproducibility in CTC enumeration using this system.

Figure 7B:
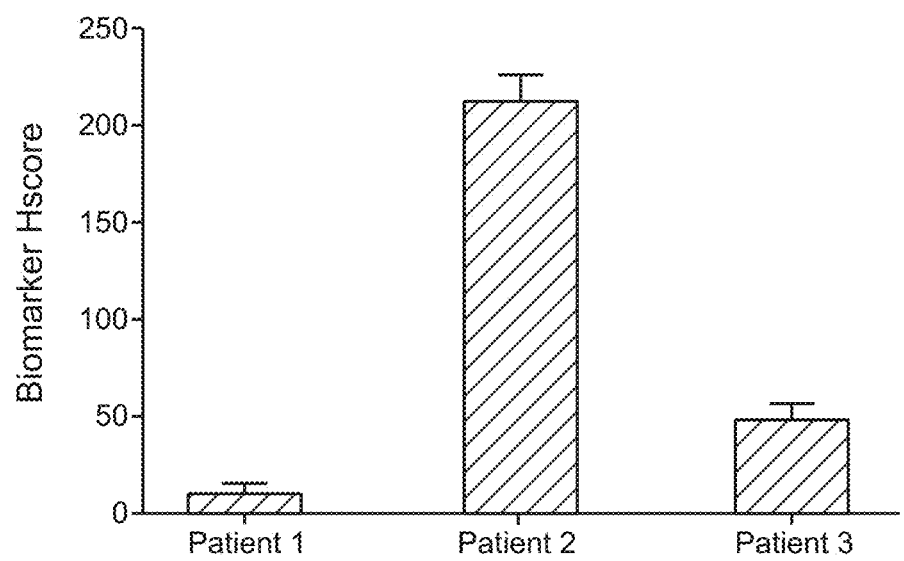

Blood samples from prostate cancer patients were drawn in duplicate before initiation of therapy (Baseline samples). Samples were analyzed on the CellSearch® system using the anti-STEAP-1 monoclonal antibody 15A5 at 20 ug/ml in the A488 channel CTC enumeration and STEAP1 expression were scored on the CellTracks analyzer, as described in Example 2. Briefly, CTCs on the CellSearch autoprep systems that showed STEAP-1 staining were selected, and were further quantified for fluorescence intensities of the anti-STEAP-1 antibody using a weighted intensity scoring system (H-score, see Example 2). Mean H-scores and STDEV were computed for each duplicate pair, and errors (+−SDEV) were plotted. As shown in FIG. 7B, there was a large dynamic range for STEAP-1 expression levels in the patient population, and further indicates tight H-scores between duplicate samples, demonstrating high reproducibility in the quantification of target expression level using the CellSearch system.

Blood samples from prostate cancer patients were drawn at 2 different time-points before initiation of therapy, Baseline 1 and Baseline 2, about 2-4 weeks apart. Blood samples were analyzed on the CellSearch® system and CTC enumeration were scored on the CellTracks analyzer, as described above. To evaluate biological variability in CTC enumeration, CTC counts were compared between the 2 baseline samples for each patient.

Figure 8:
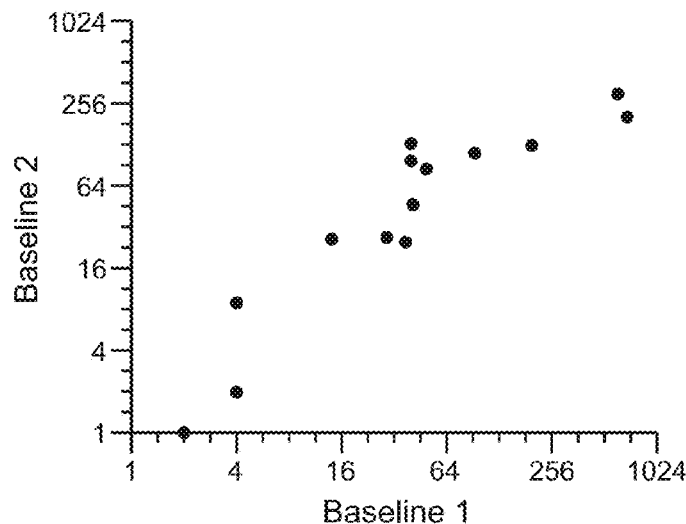
FIG. 8 depicts strong correlation in CTC enumeration from blood samples taken at baseline 1 and 2.

In FIG. 8, each dot represents a patient, with the CTCs counted at baseline 1 on the X-axis, and the CTCs counted at baseline 2 on the Y-axis. The plot includes data from 14 patients, and shows a strong correlation between CTC enumeration taken at different time point, suggesting low biological variability in CTC enumeration before initiation of the treatment. These data was used to calculate the normal variability in CTC counts, computed as the 95% Confidence Interval for the distribution of CTC counts pre-treatment.

Figure 9:
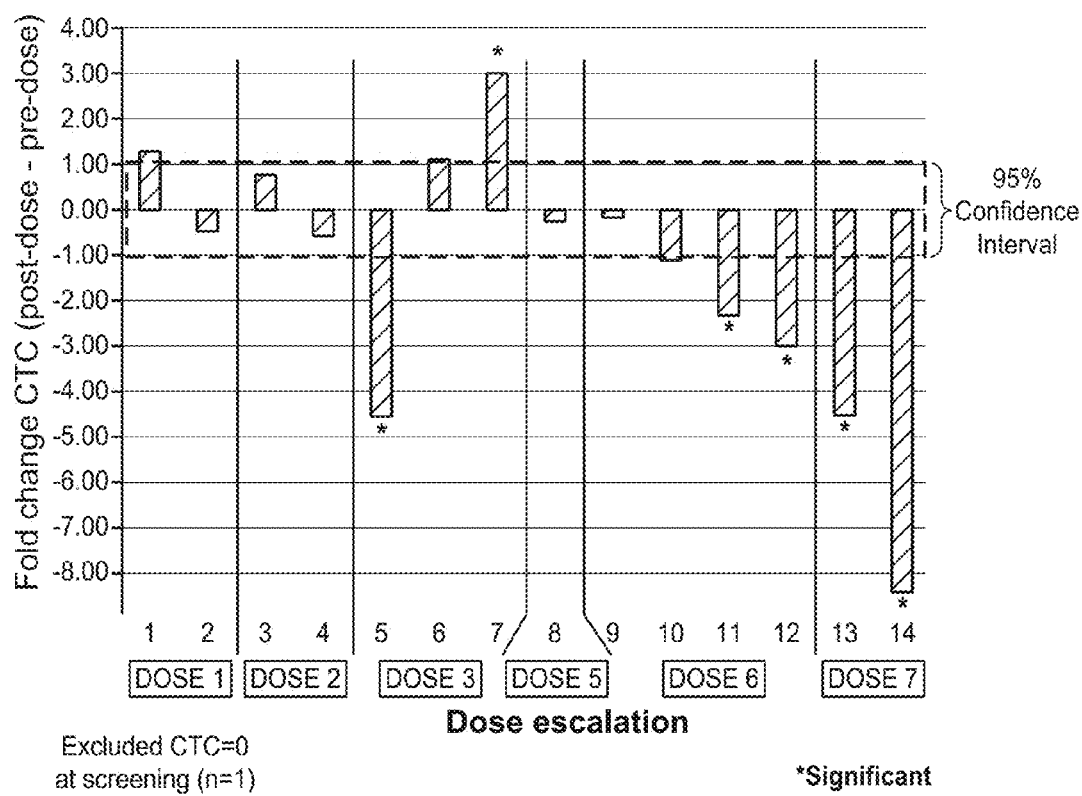
FIG. 9 depicts fold change in CTC counts of patients during dose escalation treatment from Dose 1-7 post-dose-pre-dose.
Figure 11:
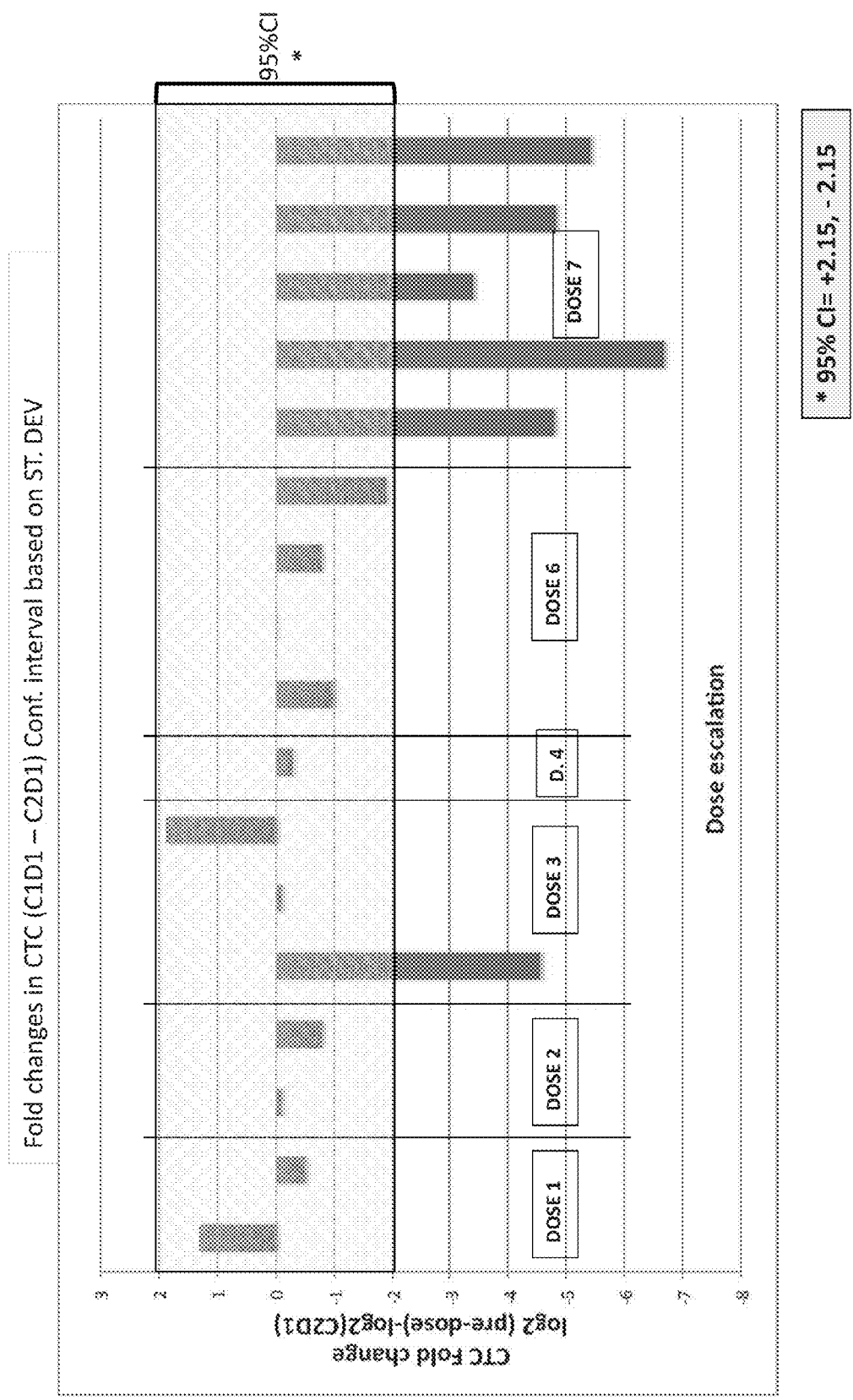
FIG. 11 depicts CTC counts of patients during dose escalation treatment from Dose 1-7 pre-dose and post-dose.

The Confidence Interval was used to determine the significance of CTC changes observed during treatment. A decrease in CTC counts above the calculated Confidence Interval was used to assess dose effects and evidence of drug activity. Blood samples from prostate cancer patients were drawn at 2 different time-points before pre-dosage of anti-STEAP1 ADC therapy and post-dosage of anti-STEAP1 ADC therapy. Samples were analyzed on the CellSearch® system, and CTC enumeration and STEAP1 expression were scored on the CellTracks analyzer as described above. As shown in FIG. 9, FIG. 10 and FIG. 11, a significant decrease in CTC counts was observed at higher dosages based on fold changes in CTC post-dosage and pre-dosage as well a favorable CTC prognostic conversion. Further, higher STEAP1 target expression was observed in patients with significant CTC decrease upon treatment (data not shown).

What is claimed is:

1. A method for diagnosing prostate cancer in a test subject, comprising:
   a) obtaining a blood sample comprising cancer cells of epithelial origin from the test subject;
   b) contacting the cancer cells of epithelial origin with an anti-STEAP1 antibody that specifically binds to the STEAP1 prostate-specific marker with a $K_D$ of ≤1000 nM;
   c) detecting whether STEAP1 is present on the cancer cells of epithelial origin by contacting the blood sample with an antibody that specifically binds to the STEAP1 prostate-specific marker antibody and detecting binding between STEAP1 and the antibody that specifically binds to the STEAP1 prostate-specific marker; and
   d) diagnosing the patient with prostate cancer when the presence of STEAP1 on the cancer cells of epithelial origin is detected;
   wherein the anti-STEAP-1 antibody is 15A5, produced by a hybridoma cell having a microorganism deposit number of PTA-12259, and
   wherein the detecting is by a method based on immunofluorescent microscopy, flow cytometry, fiber-optic scanning cytometry, or laser scanning cytometry.

2. The method of claim 1, further comprising determining the amount of the cancer cells that express the prostate-specific marker, wherein such amount is predictive of the stage of prostate cancer in the test subject.

3. The method of claim 1, further comprising determining the expression level of the prostate-specific marker on the cancer cells.

4. The method of claim 1, further comprising grading the cancer cells based on their expression level of the prostate-specific marker, and determining the percentage of the cancer cells in each grade.

5. The method of claim 1, wherein the cancer cells are identified from the blood sample with a capturing composition comprising a ligand that specifically binds to cancer cells of epithelial origin.

6. The method of claim 5, wherein the ligand is an antibody that specifically binds to an epithelial antigen preferentially expressed on cancer cells.

7. The method of claim 5, wherein the identified cancer cells are enriched in a cell fraction separated from the blood sample.

8. The method of claim 7, wherein the cell fraction is separated under a magnetic field.

9. The method of claim 8, wherein the ligand in the capturing composition is coupled to a magnetic particle.

10. The method of claim 1, wherein the anti-STEAP-1 antibody is conjugated with a first detectable label.

11. The method of claim 1, wherein the cancer cells are identified with one or more reagents that allow detection of cancer cells of epithelial origin.

12. The method of claim 11, wherein the reagents comprise a ligand that specifically binds to a cytokeratin, and wherein the ligand is optionally conjugated with a second detectable label.

13. The method of claim 12, wherein the reagents further comprise a dye that differentiates cells from non-cell components.

14. The method of claim 13, wherein the dye is 4',6-diamidino-2-phenylindole (DAPI).

15. The method of claim 14, wherein the reagents further comprise a ligand that specifically binds to a leukocyte marker, and wherein the ligand is optionally conjugated with a third detectable label.

16. The method of claim 15, wherein the ligand to a leukocyte marker is a CD45 antibody.

17. A method of monitoring response to a prostate cancer therapy in a test subject, comprising:
  a) contacting a first group of cancer cells of epithelial origin with an anti-STEAP1 antibody that specifically binds to a prostate-specific marker with a $K_D$ of ≤1000 nM, wherein the first group of cancer cells are from a first blood sample taken from the test subject;
  b) determining the amount of the cancer cells in the first group that express the STEAP1 prostate-specific marker and/or the expression level of the STEAP1 prostate-specific marker in the cancer cells;
  c) contacting a second group of cancer cells of epithelial origin with the anti-STEAP1 antibody that specifically binds to a prostate-specific marker with a $K_D$ of ≤1000 nM, wherein the second group of cancer cells are from a second blood sample taken from the test subject after a test period of prostate cancer therapy;
  d) determining the amount of the cancer cells in the second group that express the STEAP1 prostate-specific marker and/or the expression level of the STEAP1 prostate-specific marker in the cancer cells; and
  e) comparing the amount of the cancer cells that express the STEAP1 prostate-specific marker and/or the STEAP1 prostate-specific marker expression level as determined in b) with that in d), wherein the anti-STEAP-1 antibody is 15A5, produced by a hybridoma cell having a microorganism deposit number of PTA-12259, wherein the determining is by a method based on immunofluorescent microscopy, flow cytometry, fiber-optic scanning cytometry, or laser scanning cytometry, and wherein a decrease in the amount of the cancer cells expressing the STEAP1 prostate-specific marker and/or a decrease in the STEAP1 prostate-specific marker expression level in the cancer cells indicates a response to the prostate cancer therapy in the test subject.

* * * * *